(12) United States Patent
Mignolet et al.

(10) Patent No.: US 8,805,548 B2
(45) Date of Patent: Aug. 12, 2014

(54) HEADBAND FOR EXTERNAL OCCIPITAL NEUROSTIMULATION

(71) Applicants: Jean-Yves Mignolet, Momalle (BE); Pierre-Yves Muller, Collonge Bellerive (CH); Pierre Rigaux, Liège (BE)

(72) Inventors: Jean-Yves Mignolet, Momalle (BE); Pierre-Yves Muller, Collonge Bellerive (CH); Pierre Rigaux, Liège (BE)

(73) Assignee: STX-Med Sprl, Liege (BE)

( * ) Notice: Subject to any disclaimer, the term of this patent is extended or adjusted under 35 U.S.C. 154(b) by 0 days.

(21) Appl. No.: 13/914,096

(22) Filed: Jun. 10, 2013

(65) Prior Publication Data

US 2013/0282095 A1    Oct. 24, 2013

Related U.S. Application Data

(63) Continuation of application No. PCT/EP2011/054072, filed on Mar. 17, 2011.

(60) Provisional application No. 61/422,535, filed on Dec. 13, 2010.

(51) Int. Cl.
*A61N 1/00* (2006.01)

(52) U.S. Cl.
USPC .......................................................... 607/139

(58) Field of Classification Search
USPC .......................................................... 607/139
See application file for complete search history.

(56) References Cited

U.S. PATENT DOCUMENTS

| | | | |
|---|---|---|---|
| 3,998,213 A | 12/1976 | Price | |
| 4,537,198 A | 8/1985 | Corbett | |
| 4,816,964 A | 3/1989 | Weiss | |
| 6,563,424 B1 * | 5/2003 | Kaario | 340/572.1 |
| 2004/0039328 A1 | 2/2004 | Henley | |
| 2006/0293608 A1 | 12/2006 | Rothman et al. | |
| 2007/0276451 A1 | 11/2007 | Rigaux | |
| 2009/0082831 A1 | 3/2009 | Paul et al. | |
| 2009/0105576 A1 | 4/2009 | Do et al. | |
| 2009/0112282 A1 * | 4/2009 | Kast et al. | 607/46 |
| 2009/0210028 A1 | 8/2009 | Rigaux et al. | |
| 2010/0306902 A1 | 12/2010 | Bourque | |
| 2011/0319975 A1 * | 12/2011 | Ho et al. | 607/139 |

FOREIGN PATENT DOCUMENTS

| | | |
|---|---|---|
| CA | 2082092 A1 | 5/1993 |
| CN | 2531817 Y | 1/2003 |
| WO | WO 00/45701 A1 | 8/2000 |
| WO | WO 2006/063417 A1 | 6/2006 |

* cited by examiner

*Primary Examiner* — Robert N Wieland
(74) *Attorney, Agent, or Firm* — Reinhart Boerner Van Beuren P.C.

(57) ABSTRACT

The present invention relates to a headband for use in neurostimulation made at least partly of elastic or stretch material comprising: a hole to be located directly on the rear part of the scalp of a user, said hole being sized to fit the inion or occipital protuberantia; at least two electrodes directly attached to the headband and positioned adjacent to and symmetric about said hole, designed so that to be applied on the right and left branch of the occipital nerve respectively, once the inion is put in correspondence with said hole by the user; a connector for connecting a wearable neurostimulator to the headband, said connector being located opposite to said hole, once the headband is worn by the user and means coupled to the elastic or stretch material for electrically connecting said connector and each of said electrodes.

9 Claims, 6 Drawing Sheets

HEADBAND FOR EXTERNAL OCCIPITAL NEUROSTIMULATION

CROSS-REFERENCE TO RELATED APPLICATIONS

This patent application is a continuation of PCT/EP2011/054072, filed Mar. 17, 2011, which claims priority to U.S. Provisional Application No. 61/422,535, filed Dec. 13, 2010, the entire teachings and disclosure of which are incorporated herein by reference thereto.

FIELD OF THE INVENTION

The present invention relates to devices pertaining to the technical field of external neurostimulation.

PRIOR ART AND TECHNICAL PROBLEM

Neurostimulation is a well-known technique which consists in using electrical impulses to generate action potential on nerves. The devices are usually implantable systems similar to pacemakers.

Implantable neurostimulation is in use for treatment of headaches as migraine or cluster. It does exist for more than 10 years in the United States. The usual implantable neurostimulation technique consists in a neurostimulation applied to the occipital nerve.

Of course the implantable neurostimulators need surgery to be implanted and generate several problems linked to the invasive aspect of the technique.

In order to avoid the invasive issues STX-Med Company has developed a specific device and technique (so-called Cefaly®) to apply external neurostimulation to the head in order to treat and prevent headaches and migraines. This technique is known as external cranial neurostimulation and is the subject of two patent filings: WO 2006/063417 and US 2009/0210028.

The Cefaly® device uses a supra-orbital electrode in order to apply the neurostimulation to the upper branch of the trigeminal nerve (V1).

External cranial neurostimulation applied by means of a supra-orbital electrode does not have any action on the occipital nerve. Consequently supra-orbital neurostimulation cannot be used to treat occipital neuralgia and cannot replicate the usual occipital implantable neurostimulator. In addition external occipital neurostimulation is technically very complicated because of the hair present in the occipital region as compared with the smooth skin of the supra-orbital region.

Document CN 2531817 U discloses a set of electrodes of the "headband" type among which an occipital electrode allows stimulation of optic nerves having an afferent fibre at the back of the skull. This is not a "wet" electrode.

Several documents disclose electrode devices of the "headband" type intended for electroencephalograph (EEG), i.e. for measurement, not for stimulation:
- a self-adjusting device with rubber band (U.S. Pat. No. 3,998,213 A, CA 2 082 092 A);
- a visor cap device (WO 2000/45701 A);
- a bonnet device (U.S. Pat. No. 4,537,198 A).

Document US 2009/0105576 A discloses an electrode for EEG systems comprising a fixed part for contacting the skin with the use of gel.

Document US 2009/0082831 A1 discloses a vestibular stimulation system and method that include a housing, a power supply arranged in the housing, an electrode assembly adapted to be coupled to the housing and a controller arranged in the housing and operatively coupled to the power supply. The controller controls the delivery of energy from the power supply to the electrode assembly. A mounting assembly is coupled to the housing to mount the housing on such a user. The electrodes, which are not directly attached to the housing or to the mounting assembly, are connected to the power supply and/or the controller by wires or electrical leads.

AIMS OF THE INVENTION

The present invention aims at avoiding the drawbacks of prior art.

Particularly, a goal of the invention is to enable external neurostimulation of the occipital nerve in an easy and comfortable way using a wearable neurostimulator such as Cefaly® and solving the hair issue in the occipital region.

SUMMARY OF THE INVENTION

The present invention relates to a headband for use in neurostimulation made at least partly of elastic or stretch material comprising:
- a hole to be located directly on the rear part of the scalp of a user, said hole being sized to fit the inion or occipital protuberantia;
- at least two electrodes directly attached to the headband and positioned adjacent to and symmetric about said hole, designed so that to be applied on the right and left branch of the occipital nerve respectively, once the inion is put in correspondence with said hole by the user;
- a connector for connecting a wearable neurostimulator to the headband, said connector being located opposite to said hole, once the headband is worn by the user and
- means coupled to the elastic or stretch material for electrically connecting said connector and each of said electrodes.

Preferred or particular embodiments of the present invention further comprise one of the following features, or an appropriate combination thereof:
- each electrode comprises a flexible reservoir for containing electrically conductive gel, said reservoir being terminated with a metallic grid intended to come directly in contact with the scalp and to provide wet electrical contact without shaving;
- the headband comprises a linear piece of elastic or stretch material provided with snap fasteners for closing and adjusting the headband to the head of a user;
- at least part of the snap fasteners are metallic and participate to the electric connection between said connector and said electrodes;
- the headband is made of a front part and a rear part and is adjustable to the user's head by means of a plurality of snap fasteners located on the front part cooperating with at least one snap fastener located on the rear part, said front part covering partially said rear part;
- the rear part comprises an extension designed so that to prevent electrical contact between the unused snap fasteners of the front part and the user's head in the covering region of the front and rear parts;
- the headband is made of one single part provided with insulating snap fasteners intended to adjust the headband to the user's head by folding of the latter on itself.

The invention also relates to a neurostimulation device comprising a headband as above and a wearable external cranial neurostimulator attached to said connector, the wearable neurostimulator being preferably a wireless neurostimulator.

The invention also relates to a method for external occipital neurostimulation using an external cranial neurostimulation device as above, characterised at least by the following steps:
- either closing the headband around the head of the user by use of snap fasteners;
- or adjusting the headband to the diameter of the head by use of other snap fasteners providing folding of the elastic or stretch material;
- using fingers for further adjusting the headband by putting the hole of the headband in front of the inion or occipital protuberantia;
- providing electric contact between the electrodes and the skin through the scalp, by pushing onto the respective reservoirs to let gel spread out of said reservoirs through their respective grids;
- connecting the wearable external cranial neurostimulator to the connector;
- powering the wearable neurostimulator to provide neurostimulation.

SHORT DESCRIPTION OF THE DRAWINGS

FIG. 1 schematically represents a rear view of an embodiment of the headband according to the present invention.

FIG. 2 schematically represents the gel reservoir of the headband according to the present invention, with the metallic grid through which the gel can be spread out.

DETAILED DESCRIPTION OF THE INVENTION AND PREFERRED EMBODIMENTS

Four main parts are involved in this invention:
- electrode technology: use of gel that goes through a metallic grid;
- electrodes positioning: correct positioning obtained easily on the back of the skull;
- adjustable device: system foreseen to adapt to different headsizes;
- contact with a wearable device: the system can be used with the Cefaly® device.

The invention is basically a headband that enables electrical contact between a neurostimulator and the back of the skull.

Electrode Technology

Figure 1:
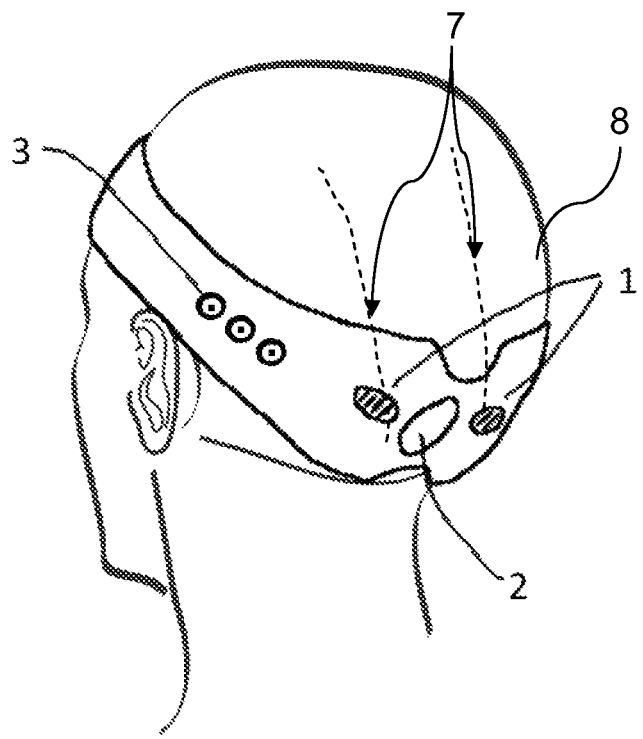
Figure 2:
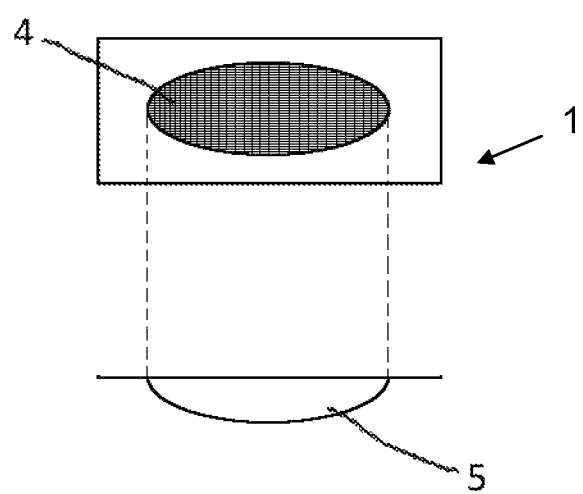

To avoid that someone has to shave the hair on the back of the skull, where the electrodes should contact the skin, the electrodes are made of high viscosity conductive gel. This gel can go through the hair, enabling a good contact with the skin. The gel should be spread on the right part of the skull. To adequately place the gel on the head, the user puts the gel first in a small reservoir 1 located on the headband (FIG. 1). The reservoir 1 is made of a container 5 closed with a grid 4 made of metallic material (FIG. 2). The user can then fit the headband on the head (see positioning below).

Figure 10:
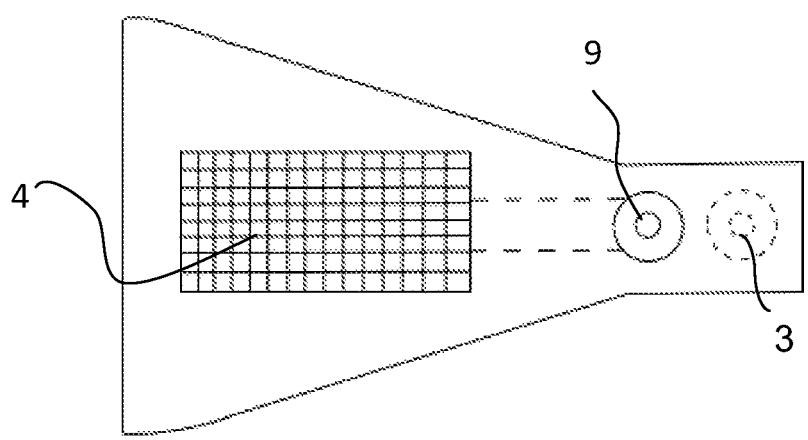
FIG. 10 represents the electrode used in the second preferred embodiment.
Figure 11:
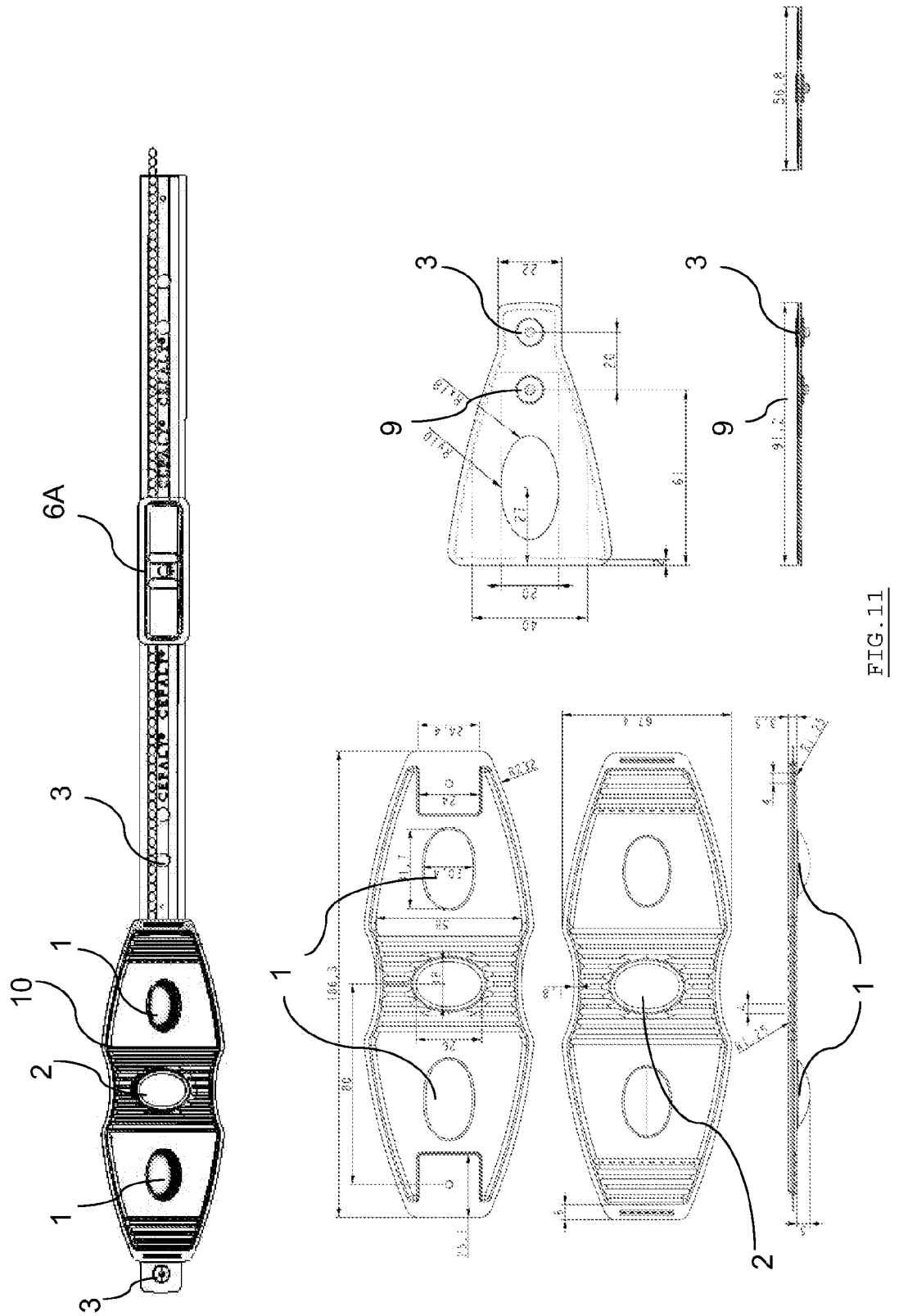
FIG. 11 represents more detailed views of the second preferred embodiment, reducing constructively the invention to practice.

During this stage, no gel is spread out, preventing any gel sitting at a wrong location. Once the system is in place, the user pushes on the back of the reservoir to spread out the gel on the head through the grid. This way no gel is spread out outside of the desired zone. The electrical conductivity is ensured by the grid 4 which is electrically connected to the stimulator via the headband thanks to a snap fastener 9 (see FIG. 7 and FIG. 10).

The grid 4 has therefore the ability to prevent the gel to spread out when it is not desirable, and to allow to spread it out at the right location when necessary. Moreover, the fact that the grid is made at least partially of conductive element enables the electrical signal to reach the skull through the gel.

Electrodes Positioning

The electrodes should be sitting on the back of the head; it is therefore difficult for a user to place them correctly. However the correct positioning of the electrodes is very important to ensure an efficient neurostimulation applied exactly on the great occipital nerve 7 (see FIG. 1). To ease this process, a hole 2 is foreseen on the back of the headband so that the user is able to place the electrodes at the right position (FIG. 1). The hole 2 should be placed exactly in front of the occipital protuberantia (inion or proteberantia occipitalis externa). It is a very good landmark, as the occipital protuberantia surfaces the base of the skull. Using a finger through the hole, the user can therefore easily locate the occipital protuberantia and thereby correctly position the headband on the head.

Adjustable Device

Not every user has the same head size. The headband should therefore be adjustable and advantageously made at least partly of elastic or stretch material. Two challenges are faced in the present invention:
1. the headband should be adjusted before it is placed on the head, to prevent difficult positioning and spread out of gel;
2. there should be an electrical contact between the front part and the back part.

The adjustments should moreover be symmetrical: the center piece of the front part should stay in the middle of the forehead, while the center hole of the back part should stay in the middle of the back of the skull.

Figure 4:
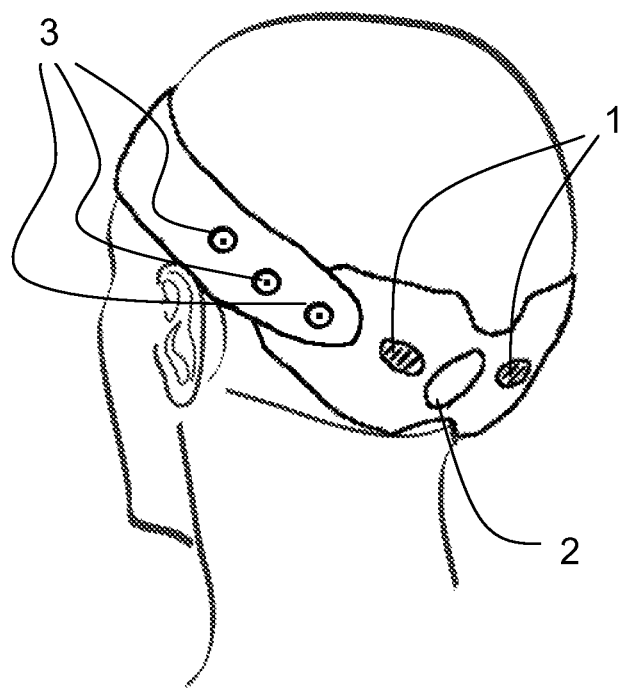
FIG. 4 represents a rear view of a first preferred embodiment of the headband according to the invention, comprising two parts connected with metallic snap fasteners.
Figure 5:
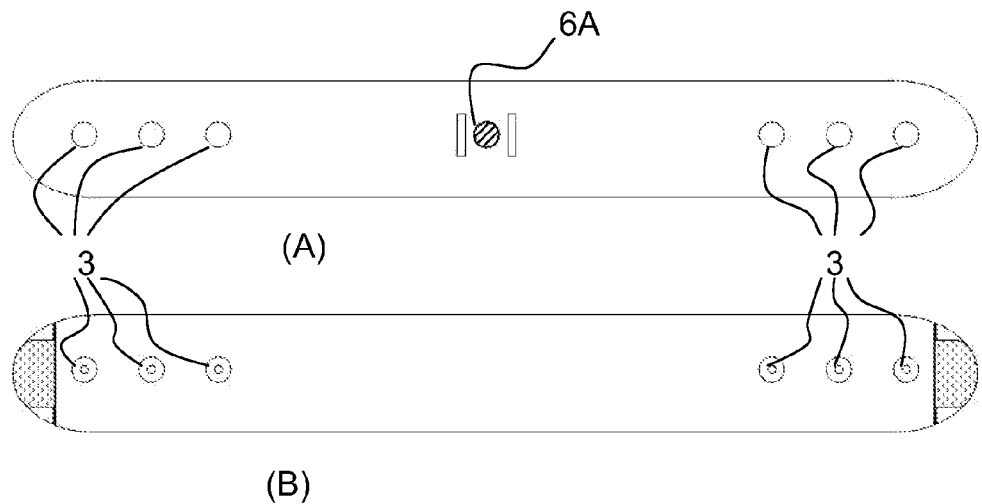
FIG. 5 represents both sides of the front part of the first preferred embodiment.
Figure 6:
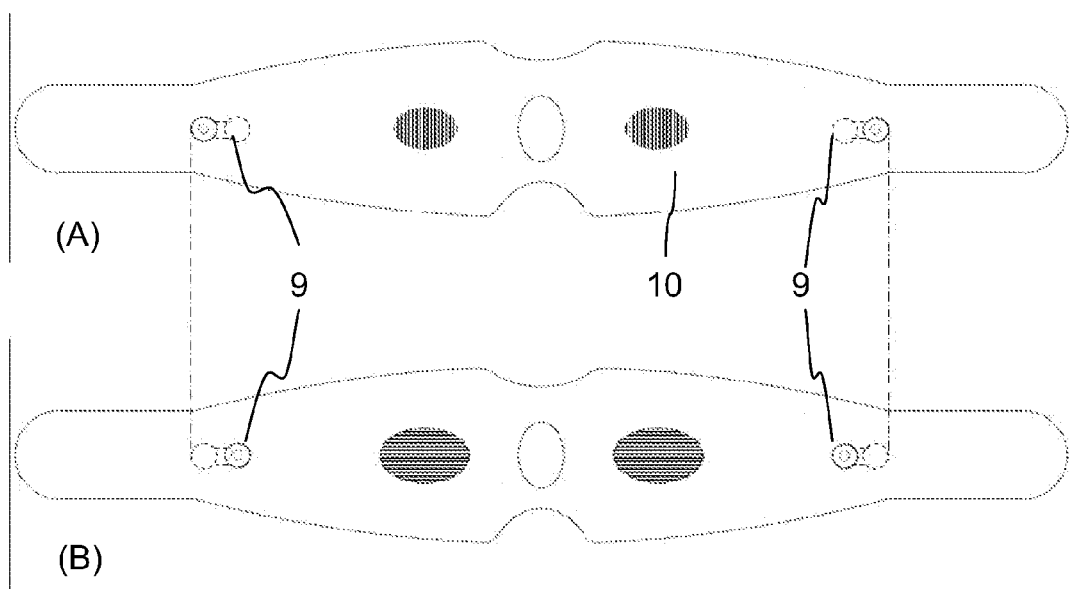
FIG. 6 represents both sides of the rear part of the first preferred embodiment.
Figure 7:
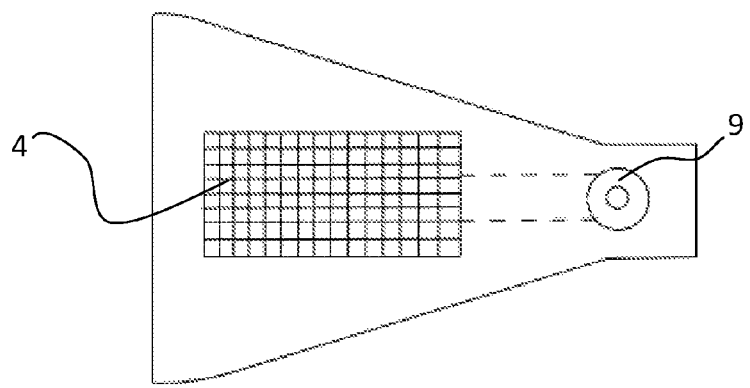
FIG. 7 represents the electrode used in the first preferred embodiment.
Figure 8:
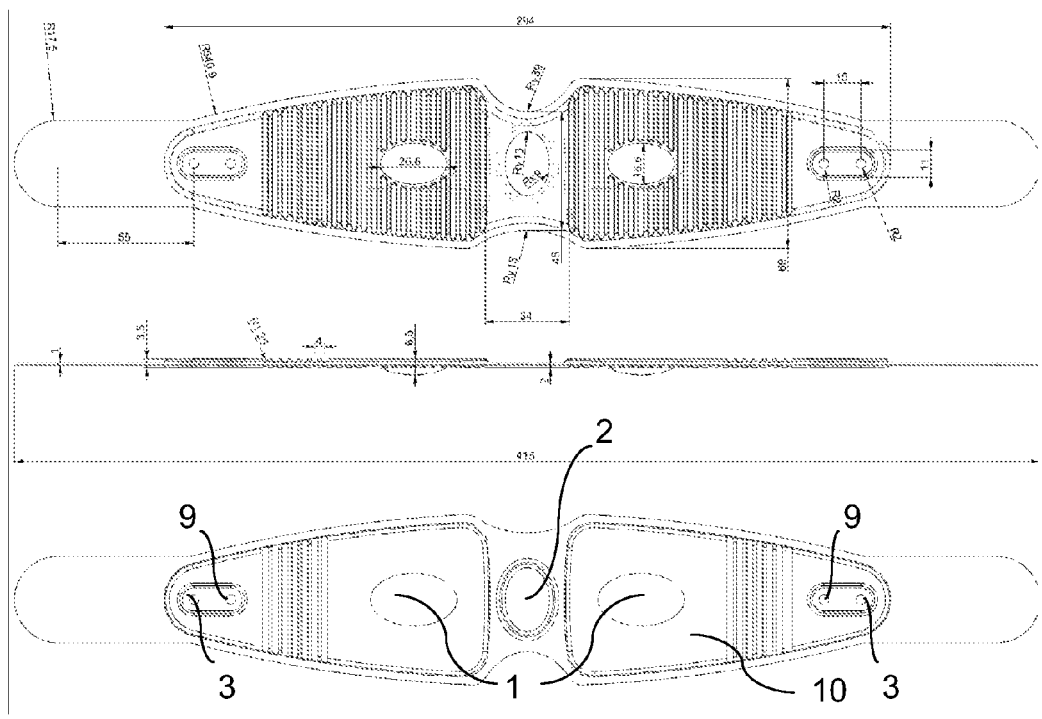
FIG. 8 represents more detailed views of the first preferred embodiment, reducing constructively the invention to practice.

To achieve this, in a first preferred embodiment (FIG. 4), two parts are adjusted one over the other. The adjustment of the headband is obtained thanks to snap connectors and an extension of the stretch material covering unused connectors. A front part (FIG. 5) contains a loose electrical wire (not shown) that is connected to a wearable device connector 6A on the front side (FIG. 5A) and to one or more snap fasteners 3 on the back side (FIG. 5B). Each snap fastener 3 is advantageously metallic, allowing electricity to go through it. A rear part (FIG. 6) comprising the electrodes 1 connects to each side of the front part through one of the snap fasteners 3 (FIG. 6A). The symmetry is ensured by a similar positioning of the snaps 3 on both sides of the band. On the rear part, an electrical wire connects a corresponding snap fastener 3 to a metallic snap fastener 9, that is to be connected to the electrode 1 (FIG. 6B, 7). Of course, snap 9 is electrically insulated on its side contacting the scalp. The rear part contains an extended part at both sides that conveniently covers the unused snap fasteners 3 to prevent wrong electric contact with the user's head.

Figure 9:
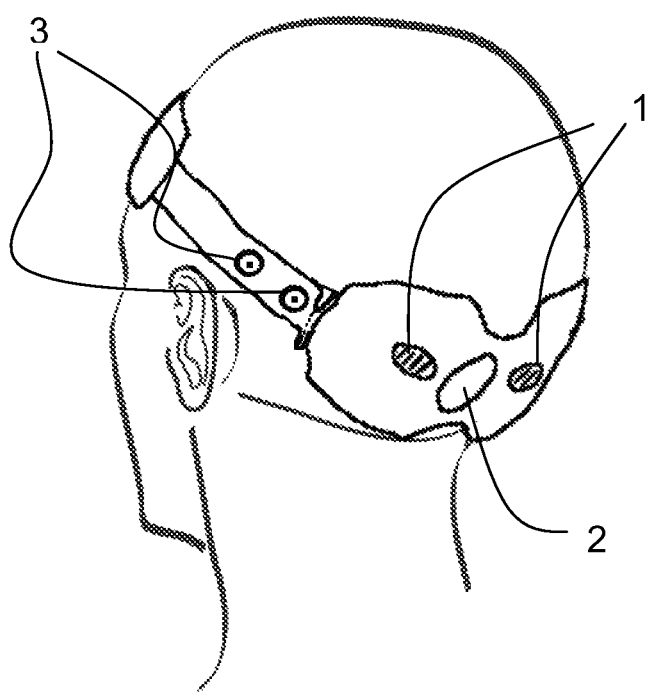
FIG. 9 represents a rear view of a second preferred embodiment of the headband according to the invention, built in one single part wherein the adjustment is performed with plastic snap fasteners.

In a second preferred embodiment (FIG. 9), the headband is made of one single piece of stretch material and contains an elastic electrical wire located within the elastic band. This electrical wire is connected directly to the electrode (FIG. 10), thanks to a metallic snap fastener 9. Adjustment snap fasteners 3 are non-metallic, for example are made of plastic, and serve the only purpose of adjustment. The symmetry is then ensured by a similar positioning of the snaps 3 on both sides of the band. The adjustment of the band to the head of the user thanks to the snaps 3 is achieved by folding of the band on itself.

All the materials known of or considered appropriate for the skilled person can be used in the above embodiments of the invention. In particular the band may be made of any suitable kind of elastic or stretch fabric while the grid may be made of any suitable metal. For example, in the first preferred embodiment of the invention, the front part is made of Lycra® and the rear part is made of thermoformed foam covered with Lycra®. The grid of the electrodes is made of stainless steel.

Wearable Stimulator

Figure 3:
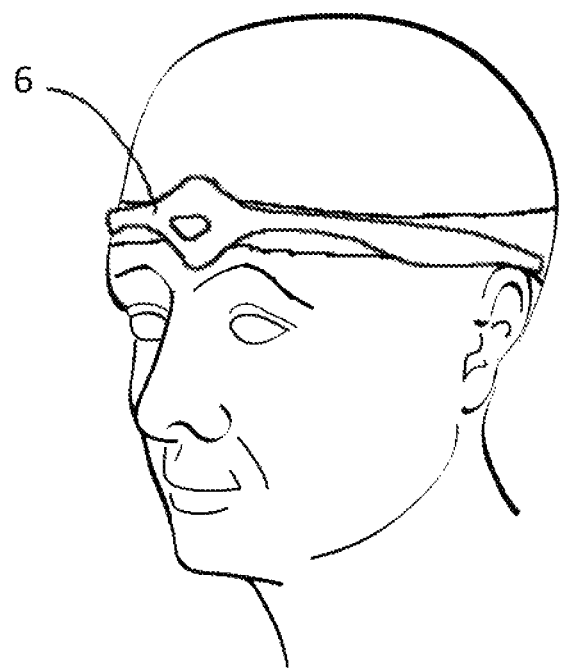
FIG. 3 represents the front connection of a wearable wireless electronic apparatus to the aforementioned headband.

The headband according to the invention provides appropriate connection 6A with a wearable stimulator 6 (FIG. 3). For example, in an embodiment very similar to the Cefaly® device itself, the mechanical attachment of the stimulator to the headband may be provided by use of a non-conductive part having the shape of a pin, while the stimulator 6 and the connector 6A on the headband are provided with means for assuring continuity of the electric contact.

REFERENCE SYMBOLS 1. electrode
2. occipital hole
3. snap fastener
4. grid
5. gel container (reservoir)
6. wearable neurostimulator; 6A connector
7. great occipital nerve
8. scalp
9. electrode snap fastener
10. electrode holder

The invention claimed is:

1. A Headband for use in neurostimulation made at least partly of elastic or stretch material comprising:
   the headband defining (2) to be located directly on the rear part of the scalp (8) of a user, said hole being sized to fit the inion or occipital protuberantia;
   at least two electrodes (1) directly attached to the headband and positioned adjacent to and symmetric about said hole (2), designed so that to be applied on the right and left branch of the occipital nerve (7) respectively, once the inion is put in correspondence with said hole (2) by the user;
   a connector (6A) for connecting a wearable neurostimulator (6) to the headband, said connector (6A) being located opposite to said hole (2), once the headband is worn by the user;
   means coupled to the elastic or stretch material for electrically connecting said connector (6A) and each of said electrodes (1); and
   wherein each electrode (1) comprises a flexible reservoir (5) for containing electrically conductive gel, said reservoir being terminated with a metallic grid (4) intended to come directly in contact with the scalp (8) and to provide wet electrical contact without shaving.

2. The Headband according to claim 1, characterised in that it comprises a linear piece of elastic or stretch material provided with snap fasteners (3) for closing or adjusting the headband to the head of the user.

3. The Headband according to claim 2, characterised in that at least part of the snap fasteners (3) are metallic and participate to the electric connection between said connector (6A) and said electrodes (1, 9).

4. The Headband according to claim 3, characterised in that the headband is made of a front part and a rear part and is adjustable to the user's head by means of a plurality of snap fasteners (3) located on the front part cooperating with at least one snap fastener (3) located on the rear part, said front part covering partially said rear part.

5. A Neurostimulation device comprising a headband according to claim 1, and a wearable external cranial neurostimulator (6) attached to said connector (6A).

6. The Neurostimulation device according to claim 5, characterised in that the wearable neurostimulator (6) is a wireless neurostimulator.

7. A Headband for use in neurostimulation made at least partly of elastic or stretch material comprising:
   the headband defining (2) to be located directly on the rear part of the scalp (8) of a user, said hole being sized to fit the inion or occipital protuberantia;
   at least two electrodes (1) directly attached to the headband and positioned adjacent to and symmetric about said hole (2), designed so that to be applied on the right and left branch of the occipital nerve (7) respectively, once the inion is put in correspondence with said hole (2) by the user;
   a connector (6A) for connecting a wearable neurostimulator (6) to the headband, said connector (6A) being located opposite to said hole (2), once the headband is worn by the user;
   means coupled to the elastic or stretch material for electrically connecting said connector (6A) and each of said electrodes (1);
   wherein the headband further comprises a linear piece of elastic or stretch material provided with snap fasteners (3) for closing or adjusting the headband to the head of the user;
   wherein at least part of the snap fasteners (3) are metallic and participate to the electric connection between said connector (6A) and said electrodes (1, 9);
   wherein the headband is made of a front part and a rear part and is adjustable to the user's head by means of a plurality of snap fasteners (3) located on the front part cooperating with at least one snap fastener (3) located on the rear part, said front part covering partially said rear part; and
   wherein the rear part comprises an extension designed so that to prevent electrical contact between the unused snap fasteners (3) of the front part and the user's head in the covering region of the front and rear parts.

8. A Headband for use in neurostimulation made at least partly of elastic or stretch material comprising:
   the headband defining (2) to be located directly on the rear part of the scalp (8) of a user, said hole being sized to fit the inion or occipital protuberantia;
   at least two electrodes (1) directly attached to the headband and positioned adjacent to and symmetric about said hole (2), designed so that to be applied on the right and left branch of the occipital nerve (7) respectively, once the inion is put in correspondence with said hole (2) by the user;

a connector (6A) for connecting a wearable neurostimulator (6) to the headband, said connector (6A) being located opposite to said hole (2), once the headband is worn by the user;

means coupled to the elastic or stretch material for electrically connecting said connector (6A) and each of said electrodes (1);

wherein the head band further comprises a linear piece of elastic or stretch material provided with snap fasteners (3) for closing or adjusting the headband to the head of the user; and wherein the headband is made of one single part provided with insulating snap fasteners (3) intended to adjust the headband to the user's head by folding of the latter on itself.

9. Method for external occipital neurostimulation using an external cranial neurostimulation device according to claim 5, characterised at least by the following steps:

- either closing the headband around the head of the user by use of snap fasteners (3);
- or adjusting the headband to the diameter of the head by use of other snap fasteners (3) providing folding of the elastic or stretch material;
- using fingers for further adjusting the headband by putting the hole (2) of the headband in front of the inion or occipital protuberantia;
- providing electric contact between the electrodes (1) and the skin through the scalp, by pushing onto the respective reservoirs (5) to let gel spread out of said reservoirs (5) through their respective grids (4);
- connecting the wearable external cranial neurostimulator (6) to the connector (6A);
- powering the wearable neurostimulator (6) to provide neurostimulation.

* * * * *

UNITED STATES PATENT AND TRADEMARK OFFICE
CERTIFICATE OF CORRECTION

| | | |
|---|---|---|
| PATENT NO. | : 8,805,548 B2 | Page 1 of 1 |
| APPLICATION NO. | : 13/914096 | |
| DATED | : August 12, 2014 | |
| INVENTOR(S) | : Jean-Yves Mignolet | |

It is certified that error appears in the above-identified patent and that said Letters Patent is hereby corrected as shown below:

Title page
(73) Assignee: Delete "STX-MED Sprl, Liege (BE)" and insert --"CEFALY TECHNOLOGY SPRL, Herstal (BE)"--.

In the Claims
Column 5, line 50, claim 1, --"a hole"-- should be inserted after --the headband defining--.

Column 6, line 27, claim 7, --"a hole"-- should be inserted after --the headband defining--.

Column 6, line 62, claim 8, --"a hole"-- should be inserted after --the headband defining--.

Signed and Sealed this
Twenty-fourth Day of November, 2015

Michelle K. Lee
*Director of the United States Patent and Trademark Office*